(12) United States Patent
Muramatsu (10) Patent No.: US 6,258,047 B1
(45) Date of Patent: Jul. 10, 2001

(54) THERAPEUTIC PRESSING DEVICE (76) Inventor: Yoshio Muramatsu, 11-7 Maruyamadai 1-chome, Konan-ku, Yokohama-shi, Kanagawa (JP), 233-0013

( * ) Notice: Subject to any disclaimer, the term of this patent is extended or adjusted under 35 U.S.C. 154(b) by 0 days.

(21) Appl. No.: 09/555,962
(22) PCT Filed: May 15, 1998
(86) PCT No.: PCT/JP98/02149
   § 371 Date: Jun. 7, 2000
   § 102(e) Date: Jun. 7, 2000
(87) PCT Pub. No.: WO99/59521
   PCT Pub. Date: Nov. 25, 1999
(51) Int. Cl.$^7$ .......................... A61B 5/103; A61B 5/117
(52) U.S. Cl. ............................. 600/594; 601/98; 601/115
(58) Field of Search .................................. 600/587, 594, 600/595; 601/98, 99, 115, 116, 100, 102; 482/91, 132, 133, 148, 907

(56) References Cited

U.S. PATENT DOCUMENTS

| | | | |
|---|---|---|---|
| 4,036,213 | * | 7/1977 | Gregory .................................. 600/594 |
| 4,422,448 | * | 12/1983 | Sugai et al. ............................. 601/99 |
| 5,101,835 | * | 4/1992 | Del Re ................................... 600/594 |
| 6,056,707 | * | 5/2000 | Hayashi .................................. 601/99 |
| 6,117,094 | * | 9/2000 | Fujii ...................................... 601/99 |
| 6,159,168 | * | 12/2000 | Warner et al. ........................ 600/594 |
| 6,190,338 | * | 2/2001 | Arndt .................................... 601/115 |

FOREIGN PATENT DOCUMENTS

| | | |
|---|---|---|
| 48-42590 | 6/1973 | (JP) . |
| 53-13577 | 2/1978 | (JP) . |
| 62-33837 | 2/1987 | (JP) . |
| 9-75413 | 3/1997 | (JP) . |

\* cited by examiner

Primary Examiner—Eric F. Winakur
Assistant Examiner—Charles Marmor, II
(74) Attorney, Agent, or Firm—Nixon & Vanderhye P.C.

(57) ABSTRACT

A pressing medical treatment apparatus (10) comprises a pressing section (55) for pressing the back of a human body and a detecting section (66) for detecting spinous process. The detecting section (66) includes a pressure sensitive sensor (23) for detecting spinous process, and it is movable in the plane parallel to the back of the human body by the aid of a guide section (21). The detecting section (66) is moved along vertebral column to detect spinous process of seventh cervical vertebra. Respective spinous processes of first to twelfth thoracic vertebras are detected on the basis thereof. A control unit (9) stores positions of thoracic vertebras corresponding to detection positions of respective spinous processes. The control unit (9) controls operation of the pressing section (55) on the basis of the stored position information so that predetermined thoracic vertebra (affected part) is pressed by using a roller (5). Various symptoms based on any damage of thoracic zygapophyseal joint can be treated in place of a therapist by using the medical treatment apparatus of the present invention.

15 Claims, 8 Drawing Sheets

(SIDE VIEW)      (BACK VIEW)

THERAPEUTIC PRESSING DEVICE

TECHNICAL FIELD

The present invention relates to a pressing medical treatment machine for pressing a specified region of a human body. In particular, the present invention relates to a pressing medical treatment machine for automatically detecting a specified position of thoracic vertebra and treating the cervico-omo-brachial syndrome and the low back pain by pressing the specified position.

BACKGROUND ART

As the diagnostic imaging apparatus is developed, it is now easy to diagnose various diseases. For example, it is possible to easily make diagnosis by using the diagnostic imaging apparatus for lumbar herniation of intervertebral disk, spondylolytic spondylolisthesis, spondylosis deformans, OPLL (Ossification of Posterior Longitudinal Ligament), spinal stenosis, neoplasm, and other external injuries. The causes of various diseases have been also clarified owing to the utilization of the diagnostic imaging apparatus. For example, it has been revealed that most of the diseases included in the so-called acute low back pain are caused by occurrence of any rupture in the outer layer of lumbar intervertebral disk due to repeated working and exercise or small trauma.

However, there are still diseases for which their causes cannot be clarified even when the diagnostic imaging apparatus is used. Those known as such diseases include, for example, the cervico-omo-brachial syndrome and the low back pain. There are a variety of symptoms of these diseases. The symptoms of the cervico-omo-brachial syndrome include, for example, scapular region pain, headache, facial pain, pain in lateral cervical region, pain in trapezius muscle, shoulder stiffness, tenderness, pain in shoulder, pain in upper arm, pain in forearm, pain and numbness in finger, backache, pain in spinous process of thoracic vertebra, intercostal neuralgia, pain in anterior region of neck, stuff up feeling in throat, chest pain, palpitation, tightening pain around thoracic vertebral column, pain like fracture of rib, and nuchal pain by sleeping. The symptoms of the low back pain include, for example, pain in iliac crest, gluteal region, and sacrum, lumbar myalgia, pain in spinous process of lumbar vertebra, abdominal pain, inguinal region pain, pain in hip joint, pain in femoral region, pain in knee and lower leg, bather's cramp, pain in calcaneal region, and pain and numbness in dorsal and plantar side of foot.

Figure 5:
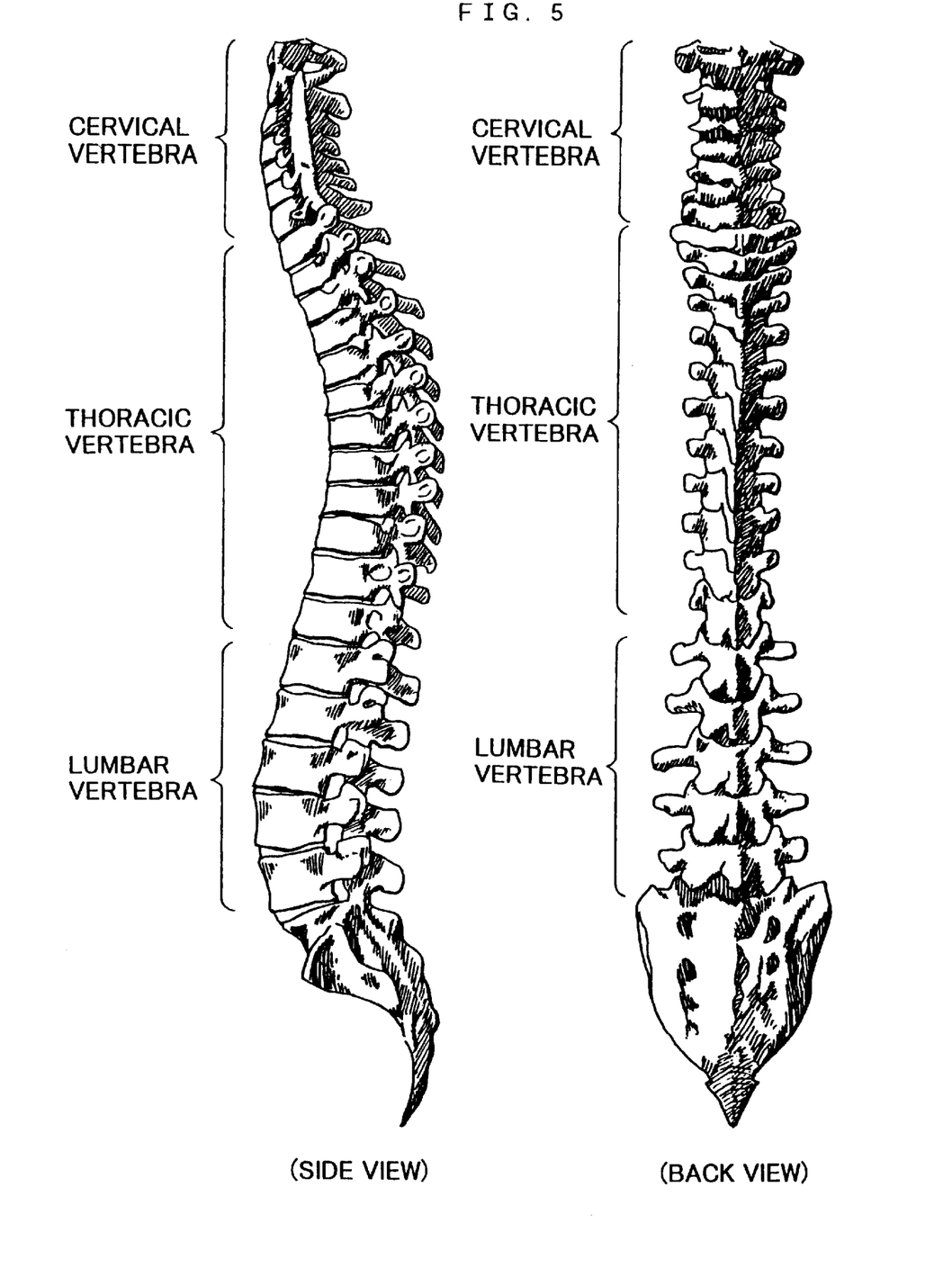
FIG. 5 shows views of the vertebral column of the human body as viewed from the side and the back.

The present inventor has practiced as a doctor and diagnosed a large number of patients having completely different symptoms such as those of the cervico-omo-brachial syndrome and the low back pain described above. During this experience, it has been noticed that a tender point (portion at which the pain is caused by being pressed) exists at a definite level between the thoracic vertebra of the human body separately from the pain region complained by the patient. It has been found that this tender point is caused by any subluxation of the zygapophyseal joint (or facet joint) between the third and fourth vertebras, between the fourth and fifth vertebras, between the tenth and eleventh vertebras, or between the eleventh and twelfth vertebras of the thoracic vertebra due to torsion, i.e., any damage of the zygapophyseal joint of the thoracic vertebra (FIG. 5 shows a side view and a back view of the vertebral column of human body for reference). Further, the tender point disappears, and the pain complained by the patient is mitigated by redressing the subluxation of the zygapophyseal joint between the third and fourth vertebras, the zygapophyseal joint between the fourth and fifth vertebras, the zygapophyseal joint between the tenth and eleventh vertebras, or the zygapophyseal joint between the eleventh and twelfth vertebras of the thoracic vertebra. Accordingly, it has been found out that the damage of the zygapophyseal joint of the thoracic vertebra is one of the causes of the cervico-omo-brachial pain and the lumber pain. Especially, the cervico-omo-brachial pain is often caused by the subluxation of the zygapophyseal joint between the third and fourth vertebras of the thoracic vertebra or the joint between the fourth and fifth vertebras of the thoracic vertebra. Further, the lumber pain is often caused by the subluxation of the zygapophyseal joint between the tenth and eleventh vertebras of the thoracic vertebra or the zygapophyseal joint between the eleventh and twelfth vertebras of the thoracic vertebra.

The present inventor has made the following medical treatment in order to redress the damage of the zygapophyseal joint of the thoracic vertebra. At first, the patient is seated on a stable chair. The left shoulder is fixed by the left hand of the therapist, while examination is made by touch with the right hand to detect the spinous processes of the third to fifth thoracic vertebras or the tenth to twelfth thoracic vertebras. The detected spinous processes of the third to fifth thoracic vertebras or the tenth to twelfth thoracic vertebras are repeatedly pressed several times. The redressment is completed by sensing the click sound by touch during the pressing treatment.

However, when the number of patients was increased, the present inventor sometimes failed to quickly respond to the requests of all of the patients, because the present inventor made the medical treatment by means of direct redressment by hand. It was indispensable to rely on the examination by touch by the therapist in order to detect the affected part, i.e., the position of the third to fifth thoracic vertebras or the tenth to twelfth thoracic vertebras. Therefore, a skillful technique was required, and it took a long time to perform the medical treatment as well.

A massage machine is known, which is used to mitigate, for example, the shoulder discomfort and the muscle fatigue by massaging or striking the back of the human body with a pressing member such as a roller and a sphere. For example, Japanese Patent Application Laid-Open No. 9-75413 discloses a massage machine for measuring hardness of muscle with a muscle hardness meter and detecting a hard region such as stiffness to perform massage in a concentrated manner. However, such a conventional massage machine discloses no means for detecting the position of the thoracic vertebra at all. Such a massage machine is used to loosen and mitigate the stiffness and the muscle fatigue, which cannot be applied to the medical treatment for the cervico-omo-brachial pain and the low back pain by redressing the damage of the zygapophyseal joint of the thoracic vertebra.

The present invention has been made taking such viewpoints into consideration, an object of which is to provide a pressing medical treatment apparatus which makes it possible to redress the damage of the zygapophyseal joint of the thoracic vertebra by pressing a specified region of the thoracic vertebra instead of a therapist.

Another object of the present invention is to provide a pressing medical treatment apparatus which makes it possible to automatically detect a specified region of the thoracic vertebra so that the specified region is pressed to treat various symptoms based on the damage of the zygapophyseal joint of the thoracic vertebra.

DISCLOSURE OF THE INVENTION

According to a first aspect of the present invention, there is provided a pressing medical treatment apparatus having a pressing member for pressing a specified region of a human body, the apparatus comprising:

a measuring unit for measuring at least one position of first to twelfth thoracic vertebras;

a pressing member-driving unit for driving the pressing member to press a back of the human body; and a control unit for controlling the pressing member-driving unit to press the measured thoracic vertebra or vicinity thereof on the basis of position information on at least one of the thoracic vertebras measured by the measuring unit. Accordingly, the specified region of the thoracic vertebra can be detected without any examination by touch to be performed by a therapist. The control unit controls the operation of the pressing member so that the pressing member is moved to the specified region of the thoracic vertebra to press the specified region on the basis of the position information on the thoracic vertebra measured by the measuring unit. Therefore, it is possible to treat a variety of symptoms based on the damage of the zygapophyseal joint of the thoracic vertebra in place of the therapist by using the medical treatment apparatus according to the present invention.

Figure 10:
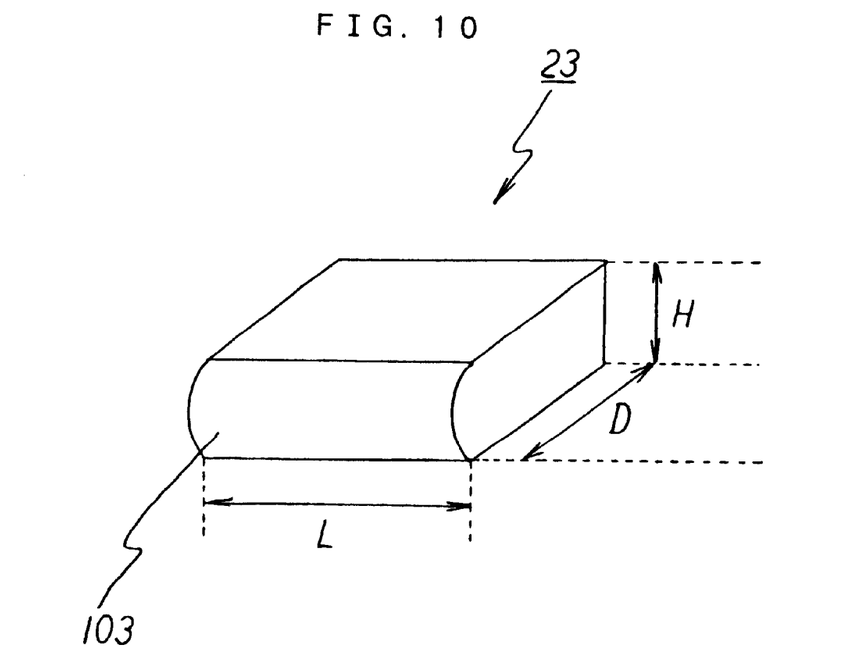
FIG. 10 shows a schematic perspective view illustrating a preferred shape of a spinous process detection sensor.

In the pressing medical treatment apparatus of the present invention, it is preferable that the measuring unit for measuring the position of at least one of the first to twelfth thoracic vertebras includes a spinous process detection sensor for detecting a spinous process of the thoracic vertebra. The spinous process detection sensor is a sensor capable of detecting the ridge corresponding to the spinous process of the thoracic vertebra at the back of the human body. For example, it is possible to use a pressure sensitive sensor composed of a piezoelectric element. In view of the object to detect the spinous process, the sensor preferably has a shape of a sensor 23 as shown in FIG. 10. The width L of the spinous process detection sensor is desirably about 3 cm considering the fact that the lateral width of the tip of the spinous process is about 1 to 1.5 cm, which is about 1.5 to 1.8 cm upon examination by touch via the body skin, and that many people are observed to have light scoliosis of the vertebral column.

Figure 8:
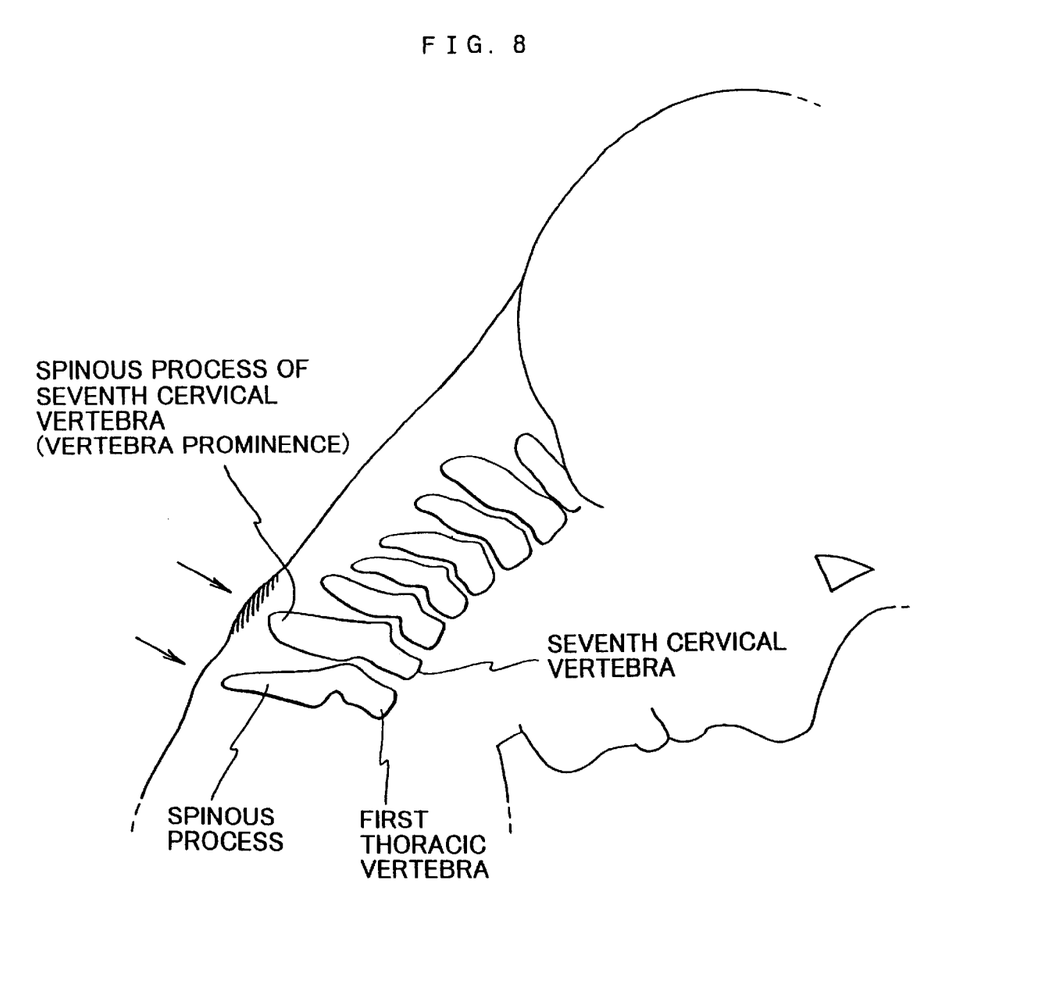
FIG. 8 shows a view of the cervical vertebra as viewed from the side in a state in which the neck is bent frontwardly.

The position of the spinous process of each of the thoracic vertebras is determined, for example, as follows by using the spinous process detection sensor. At first, the spinous process detection sensor is installed to a movement unit which is freely movable on the back surface of the human body. The neck of a patient is deeply bent frontwardly, and the spinous process detection sensor is moved from the cervical part along the vertebral column while making contact to detect the spinous process of the seventh cervical vertebra (prominent vertebra). As shown in FIG. 8, the spinous process of the seventh cervical vertebra is a region which conspicuously protrudes on the back inclined surface of the cervical part when the cervical part is deeply inclined frontwardly. Accordingly, the spinous process of the seventh cervical vertebra is easily detected by performing the detection while deeply bending the neck of the patient frontwardly as described above. As shown in FIG. 8, the first thoracic vertebra is disposed just under the seventh cervical vertebra. Therefore, the spinous processes of the first thoracic vertebra, the second thoracic vertebra, the third thoracic vertebra and so forth can be detected by further moving the spinous process detection sensor downwardly from the position of the spinous process of the seventh cervical vertebra. Thus, it is possible to obtain the position information on the spinous processes of the thoracic vertebra. When the detection sensor fails to detect all of the spinous processes of the first to twelfth thoracic vertebras, the position of the undetected spinous process of the thoracic vertebra may be estimated by means of calculation by using, for example, a calculating unit, on the basis of the position information on the successfully detected spinous process of the thoracic vertebra. The pressing member-driving unit is controlled by the control unit on the basis of the obtained position information on the spinous process of the thoracic vertebra so that the pressing member is moved to the specified region to be subjected to the pressing medical treatment to press the specified region.

Figure 6:
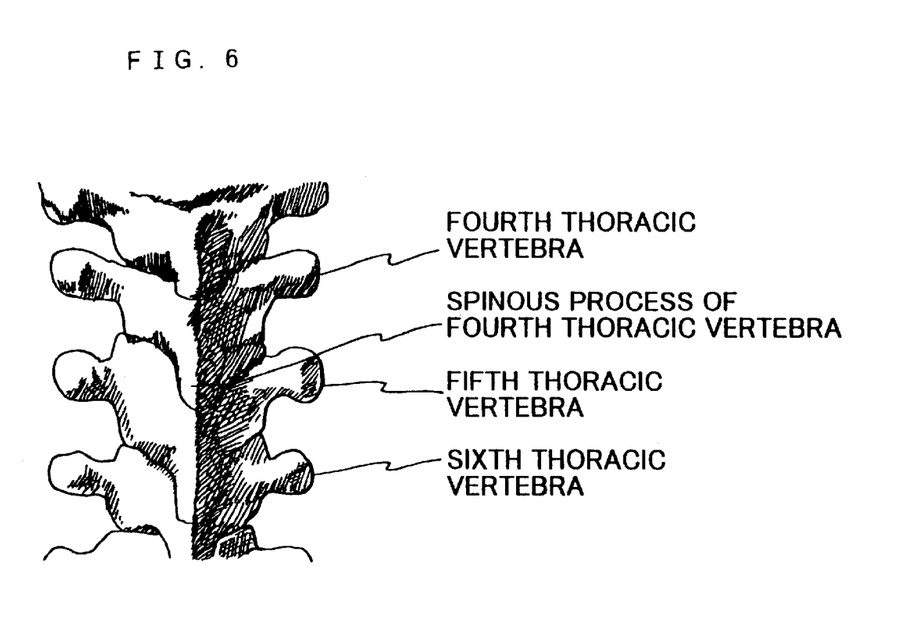
FIG. 6 shows a partial magnified back view illustrating the thoracic vertebra.
Figure 9:
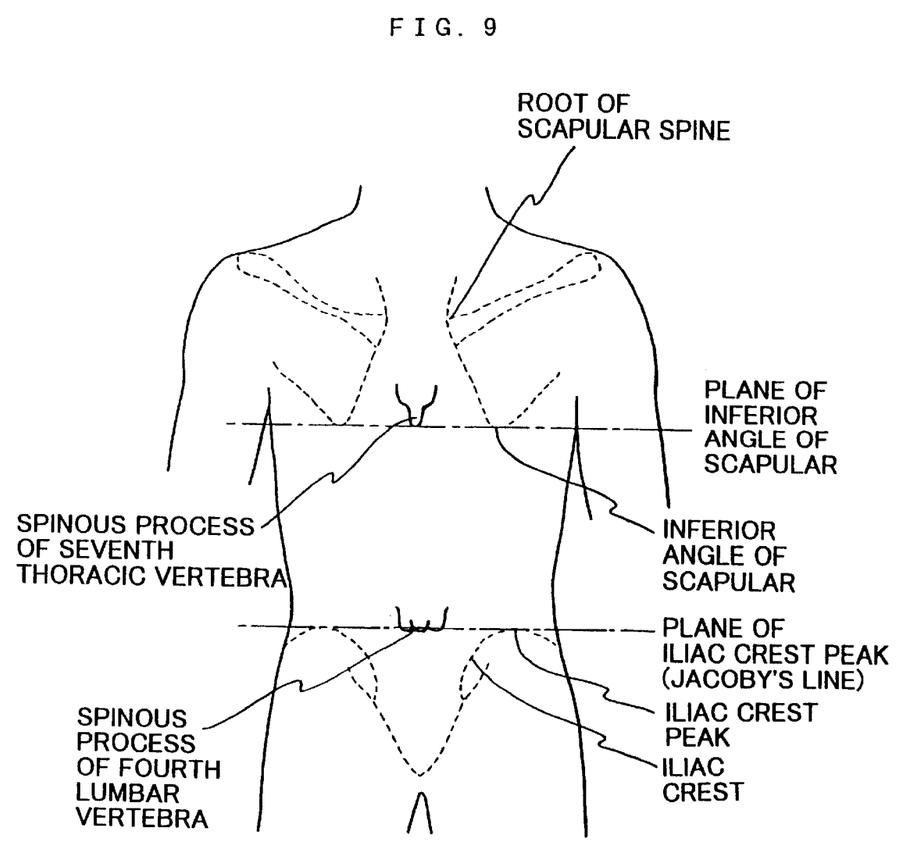
FIG. 9 shows a view of the human body as viewed from the back, illustrating the positional relationship between the inferior angle of scapular and the spinous process of the seventh thoracic vertebra and the positional relationship between the iliac crest peak and the spinous process of the fourth lumbar vertebra.

It is also preferable that the measuring unit for measuring the position of the thoracic vertebra further comprises an inferior angle of scapular detection sensor for detecting inferior angle of scapular. It is easier to measure the positions of the first to twelfth thoracic vertebras by detecting the position of the inferior angle of scapular by using the inferior angle of scapular detection sensor. That is, as shown in FIG. 9, it is known that the spinous process, which is located on the line obtained by connecting the both inferior angle of scapular (especially the centers of the both inferior angle of scapular), approximately corresponds to the spinous process of the seventh thoracic vertebra. Therefore, the right and left inferior angle of scapular are firstly detected by using the inferior angle of scapular detection sensor. The position of the spinous process of the seventh thoracic vertebra can be specified on the basis of the position information on the inferior angle of scapular. The other spinous processes of the thoracic vertebras are detected by using the spinous process detection sensor described above on the basis of the obtained position information on the spinous process of the seventh thoracic vertebra in an order starting from the spinous process of the seventh thoracic vertebra, i.e., in an order of the spinous process of the sixth thoracic vertebra, the spinous process of the fifth thoracic vertebra, the spinous process of the fourth thoracic vertebra and so forth upwardly from the spinous process of the seventh thoracic vertebra, or in an order of the spinous process of the eighth thoracic vertebra, the spinous process of the ninth thoracic vertebra, the spinous process of the tenth thoracic vertebra and so forth downwardly from the spinous process of the seventh thoracic vertebra so that the respective positions of the spinous processes of the first to twelfth thoracic vertebras may be specified. The positional relationship between the spinous process and the thoracic vertebra will be explained with reference to FIG. 6. As shown in FIG. 6, the spinous process of the fourth thoracic vertebra protrudes obliquely frontwardly from the fourth thoracic vertebra as viewed on the plane of the paper so as to cover the fifth thoracic vertebra disposed just under the fourth thoracic vertebra to which the concerning spinous process belongs. That is, assuming that the number of the thoracic vertebra is n, the position of the spinous process of the nth thoracic vertebra corresponds to the position of the (n+1)th thoracic vertebra. Therefore, the position of the spinous process, which is detected by the spinous process detection sensor, corresponds to the position of the thoracic vertebra disposed just under the thoracic vertebra to which the concerning spinous process belongs. Accordingly, it is possible to detect the position of each of the thoracic vertebras on the basis of the position information on the spinous process of each of the thoracic vertebras.

It is also preferable that the measuring unit for measuring the position of the thoracic vertebra includes an iliac crest detection sensor for detecting iliac crest. By using the sensor, it is also easy to measure the positions of the first to twelfth thoracic vertebras from the position of the iliac crest peak (uppermost end portion of the iliac crest). That is, as shown in FIG. 9, it is known that the spinous process, which is located on the line (Jacoby's line) obtained by connecting the right and left iliac crest peaks, approximately corresponds to the spinous process of the fourth lumbar vertebra. Therefore, the both iliac crest peaks are detected by using the iliac crest detection sensor, and the position of the spinous process of the fourth lumbar vertebra can be specified on the basis of the position information on the detected both iliac crest peaks. With reference to the obtained position of the spinous process of the fourth lumbar vertebra, for example, the spinous process detection sensor described above is used to detect, from the spinous process of the fourth lumbar vertebra, the spinous process of the third lumbar vertebra, the spinous process of the second lumbar vertebra, the spinous process of the first lumbar vertebra, the spinous process of the twelfth thoracic vertebra and so forth upwardly in this order. Thus, the positions of the spinous processes of the first to twelfth thoracic vertebras can be specified. As described above, the detected position of the spinous process corresponds to the position of the thoracic vertebra disposed just under the thoracic vertebra to which the concerning spinous process belongs. Accordingly, it is possible to specify the positions of the respective thoracic vertebras from the position information on the spinous processes of the respective detected thoracic vertebras. The iliac crest detection sensor and the inferior angle of scapular detection sensor may be provided commonly to the spinous process detection sensor. Thus, all of the iliac crest, the inferior angle of scapular, and the spinous process may be detected with one sensor.

Figure 7:
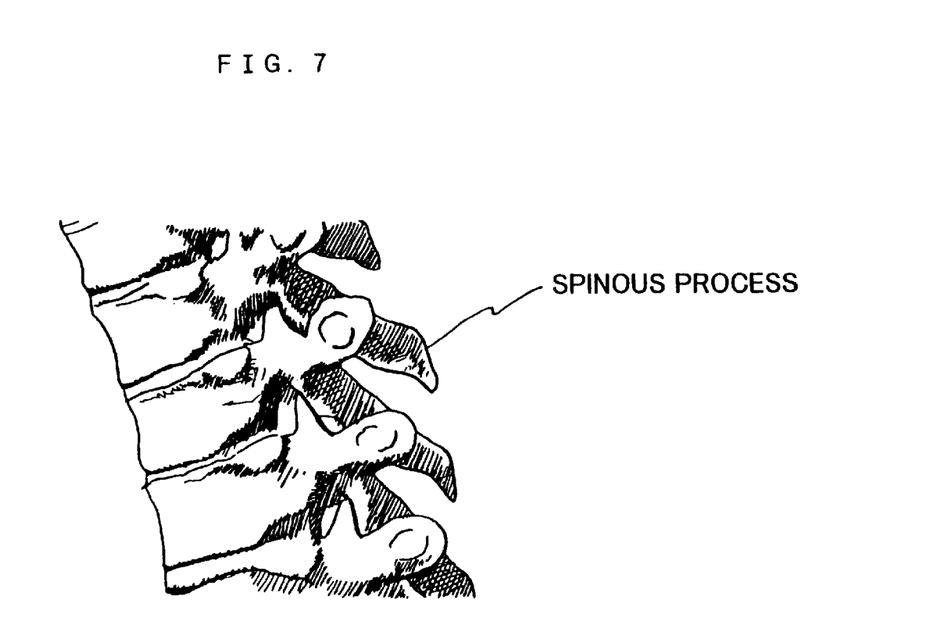
FIG. 7 shows a partial magnified side view illustrating the thoracic vertebra.

In the present invention, the back of the human body is preferably pressed along the spinous processes of the thoracic vertebras in a direction from the upper half to the lower half of the human body. FIGS. 6 and 7 show a partial magnified back view and a partial magnified side view of the thoracic vertebras shown in FIG. 5 respectively. As shown in FIGS. 6 and 7, the spinous process protrudes obliquely downwardly from the thoracic vertebra bone. Therefore, when the pressing treatment is performed as described above, the subluxation of the zygapophyseal joint of the thoracic vertebra can be redressed without damaging the spinous process of the thoracic vertebra. As described above, one of the causes of the cervico-omo-brachial pain and the low back pain is the subluxation due to any torsion of the joint between the third and fourth vertebras of the thoracic vertebra, the joint between the fourth and fifth vertebras of the thoracic vertebra, the joint between the tenth and eleventh vertebras of the thoracic vertebra, or the joint between the eleventh and twelfth vertebras of the thoracic vertebra. Therefore, as for the region to be pressed, it is desirable to press the third, fourth, and fifth thoracic vertebras, or the tenth, eleventh, and twelfth thoracic vertebras. Accordingly, it is possible to redress the subluxation of the joint between the third and fourth vertebras of the thoracic vertebra, the joint between the fourth and fifth vertebras of the thoracic vertebra, the joint between the tenth and eleventh vertebras of the thoracic vertebra, or the joint between the eleventh and twelfth vertebras of the thoracic vertebra. Thus, it is possible to mitigate or eliminate the cervico-omo-brachial pain and the low back pain.

Figure 11:
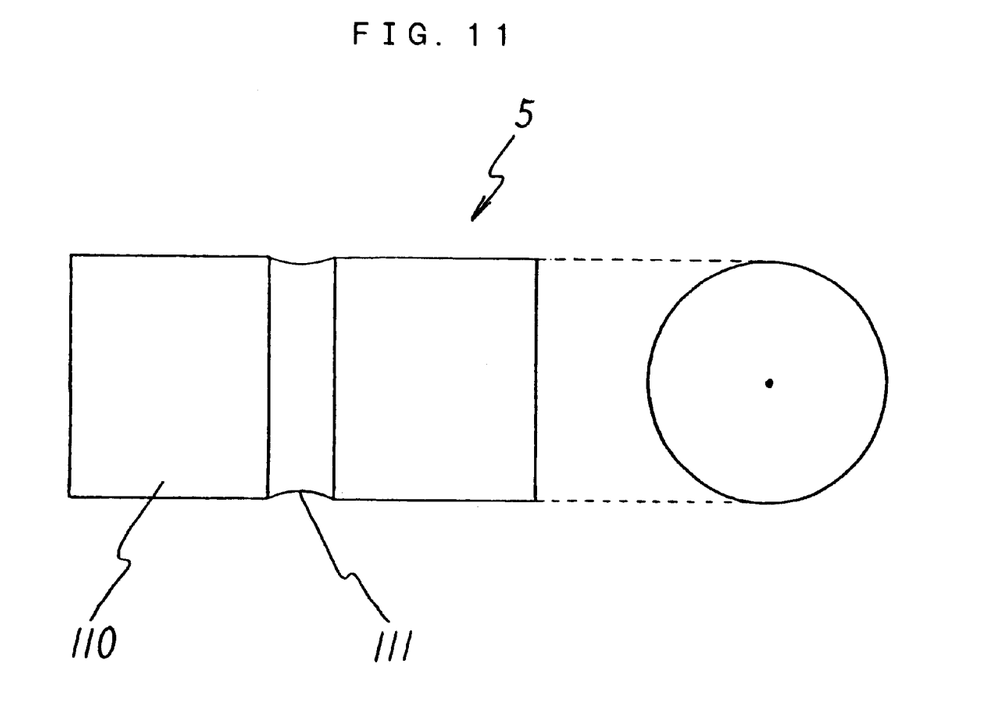
FIG. 11 shows a front view and a side view illustrating a columnar roller as a pressing member.

As for the shape of the pressing member, it is preferable to use a columnar roller 5 provided with a recess 111 on a side wall 110 as shown in FIG. 11, considering the ridge of the spinous process. The medical treatment can be performed without damaging the spinous process by pressing the specified region by allowing the recess of the pressing member having the shape as described above to coincide with the ridge of the spinous process. The mutual distance between the right and left roots of scapular spine indicated by phantom lines in FIG. 9 is 15 cm to 16 cm in the case of male, or 13 cm to 14 cm in the case of female. It is preferable that the pressing member does not contact with the root of scapular spine when the pressing treatment is performed. Considering this fact, it is preferable that the lateral width of the pressing member is about 12 cm. If a hard material is used for the material for the pressing member, then the stimulus to the affected part is too strong upon the pressing treatment, and hence the tension of the back muscle is not released due to the pain caused thereby. Therefore, the material for the pressing member is preferably a material in which at least its surface is relatively soft. For example, the pressing member is preferably formed of urethane rubber or sponge.

It is preferable that the pressing medical treatment apparatus of the present invention further comprises a support member for supporting the human body at a position in front thereof. Accordingly, even when the back of the human body is pressed with the pressing member, it is possible to avoid the reduction of the pressing force on the back of the human body, which would be otherwise caused by the frontward movement of the human body. The pressing medical treatment apparatus may further comprise a seat section so that the medical treatment is performed in a state in which the patient is seated thereon. The medical treatment in the seated state is extremely effective on the patient who is difficult to perform the action of supine, recumbency, and standing up and sitting down. It is also preferable to adopt a form in which the pressing medical treatment apparatus of the present invention is incorporated into a bed, and the medical treatment is performed in a state in which the patient is allowed to lie facing upward on the bed.

According to a second aspect of the present invention, there is provided a pressing medical treatment apparatus having a pressing member for pressing a specified region of a human body, the apparatus comprising:

a mark for being attached to the specified region of the human body;

a detecting unit for detecting the mark;

a pressing member-driving unit for driving the pressing member; and a control unit for controlling the pressing member-driving unit on the basis of position information on the mark detected by the detecting unit.

In the present invention, the region to be pressed is previously specified by means of examination by touch by a therapist. The mark is affixed to the specified region, and the mark is detected by using the detecting unit. The pressing member-driving unit is controlled by the control unit so that the pressing member is moved to the detected mark position, i.e., to the position to be pressed to perform the pressing medical treatment. More specifically, the region, which causes the cervico-omo-brachial pain and the low back pain, i.e., the position of the joint between the third and fourth vertebras, the joint between the fourth and fifth vertebras, the joint between the tenth and eleventh vertebras, or the joint between the eleventh and twelfth vertebras of the thoracic vertebra, can be quickly determined by means of the examination by touch performed by the skillful therapist. The mark is attached thereto. The mark is detected by the medical treatment apparatus of the present invention. The cervico-omo-brachial pain and the low back pain can be easily treated by pressing the concerning region with the pressing member. In the second aspect of the present invention, the specified region to be treated (tender point) is detected by the therapist, and the pressing treatment is performed by the controlled medical treatment apparatus. This aspect is effective when the tender point is difficult to be found, when a plurality of tender points exist, or when the patient is in a series case. Further, it is possible to provide a cheap medical treatment apparatus, because the spinous process detection sensor is unnecessary.

Those usable as the mark to be attached to the back of the human body include, for example, seals composed of a material having a heat-insulating property, seals having a light-reflecting property, and seals composed of a magnetic material. It is desirable that the detecting unit for detecting the mark is selected in accordance with the characteristic of the mark. For example, when the mark has the heat-insulating property, it is preferable to use, as the detecting unit, a sensor such as an infrared ray sensor capable of detecting the heat. When the mark having the heat-insulating property is stuck to the specified region at the back of the human body, the thermal radiation is decreased only at the portion of the back of the human body to which the mark is attached. Therefore, the mark position, i.e., the specified region can be specified by moving the infrared ray sensor over the back of the human body to detect the portion at which the temperature is low. When the mark to be attached to the back of the human body is the seal having the light-reflecting property, for example, an optical detecting unit, which is provided with a light-radiating section and a light-detecting section, is used as the detecting unit. The mark position is preferably specified by detecting the reflected light from the mark with the light-detecting section while radiating the light onto the back of the human body with the light-radiating section. When the mark composed of the magnetic material is attached to the back of the human body, it is preferable to use, as the detecting unit, a magnetic sensor capable of detecting the magnetism. The mark position can be specified by detecting the magnetism from the mark.

BEST MODE FOR CARRYING OUT THE INVENTION

Embodiments of the present invention will be specifically explained below with reference to the drawings. However, the present invention is not limited thereto.

First Embodiment

Figure 1:
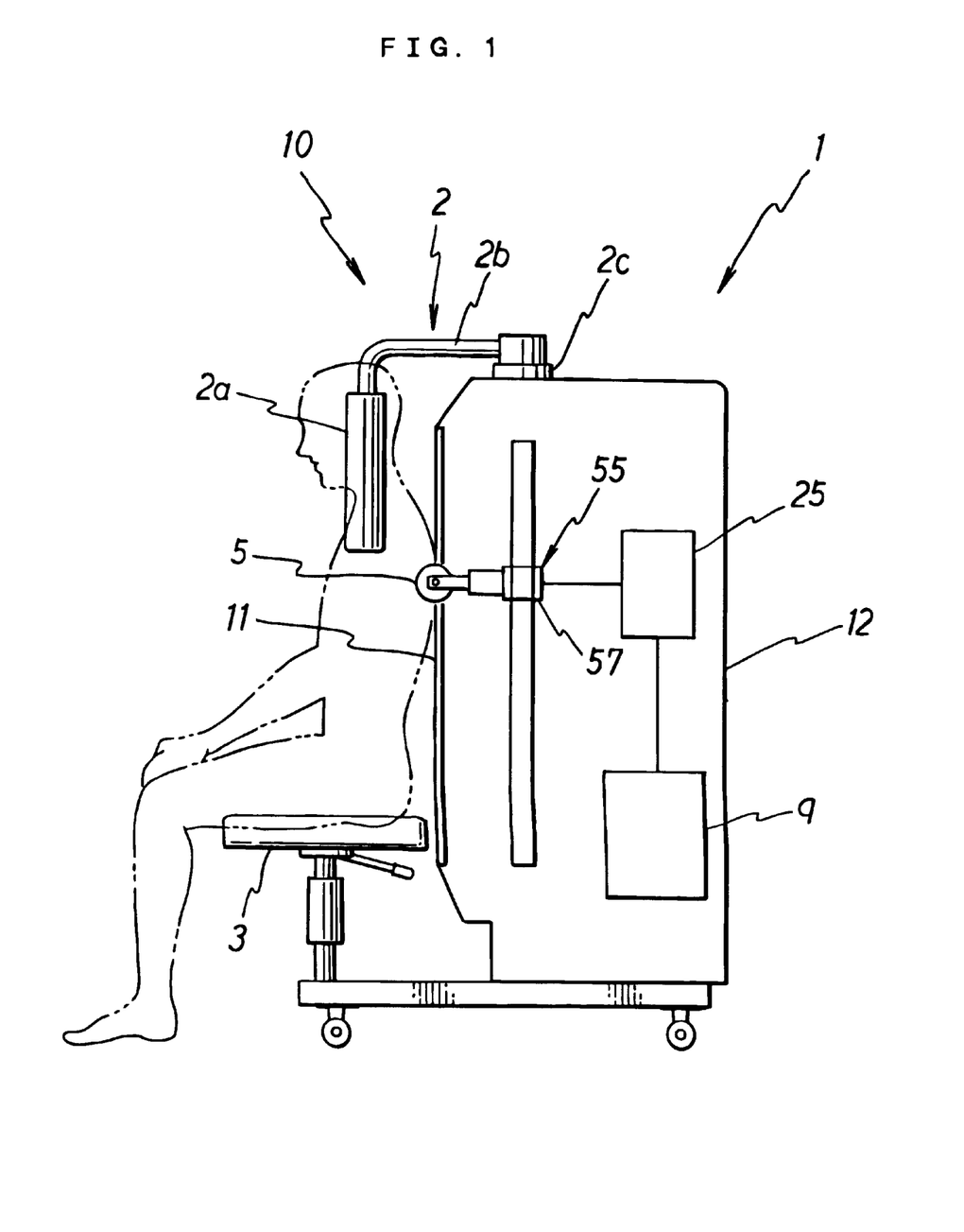
FIG. 1 shows a schematic arrangement of a pressing medical treatment apparatus according to the present invention.

FIG. 1 shows a schematic arrangement of a pressing medical treatment apparatus according to the present invention. The pressing medical treatment apparatus 10 principally comprises a main body 1, a shoulder holder 2 attached to the main body 1, and a seating chair 3.

The shoulder holder 2 includes a pair of arms 2b attached rotatably to bearings 2c formed on the upper surface of the main body 1, and holding sections 2a composed of an elastic member such as urethane rubber installed to tips of the arms 2b respectively. As shown in the drawing, each of the arms 2b extends horizontally from the main body 1, and then it is bent downwardly. The holding sections 2a hold both shoulders of a patient at front positions. Each of the arms 2b is rotatable about the center of the bearing 2c. The shoulder of the patient is released from the holding sections 2a by rotating the arms 2b in the lateral directions of the main body so that the arms 2b are separated from each other. Each of the horizontal section and the vertical section of the arm 2b may have a structure which is expandable in conformity with the body size of the patient.

The seating chair 3 includes, under its seating surface, a mechanical expandable mechanism based on a ball screw or a pneumatic system composed of, for example, a piston and a cylinder. The seating surface is vertically movable in conformity with the length of the lower leg of the patient.

Figure 2:
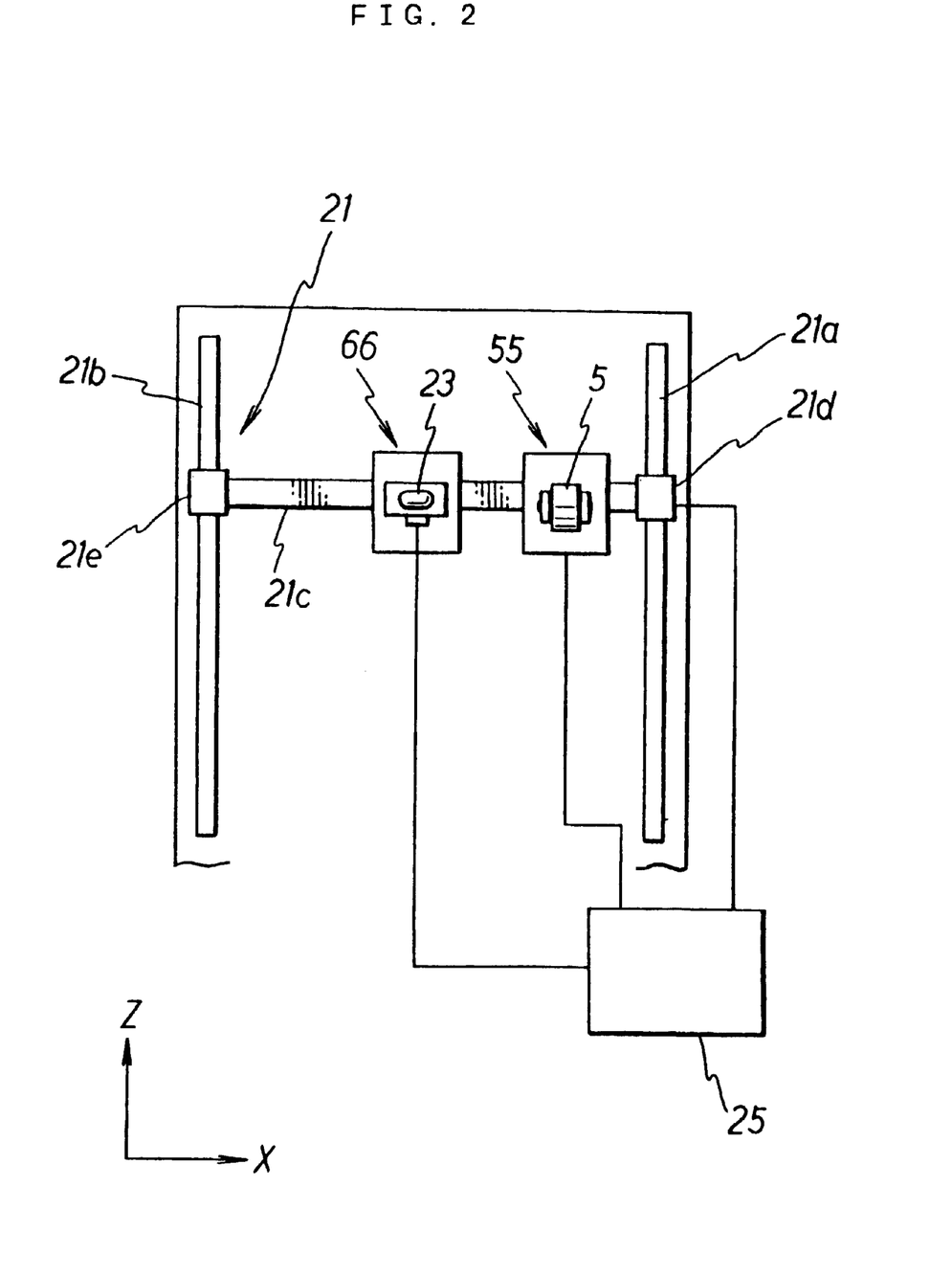
FIG. 2 shows a schematic arrangement of a measuring unit for measuring the position of the thoracic vertebra.

The main body 1 principally comprises a pressing section 55 for pressing the back of the human body, a detecting section 66 for detecting the position of the specified region to be pressed (see FIGS. 2 and 4), a control unit (microcomputer) 9 for controlling the operation of the pressing section 55 and the detecting section 66, a guide section 21 for moving the pressing section 55 and the detecting section 66 in a plane parallel to the back of the human body, and a frame 12 on which the guide section 21 is fixed.

Figure 3:
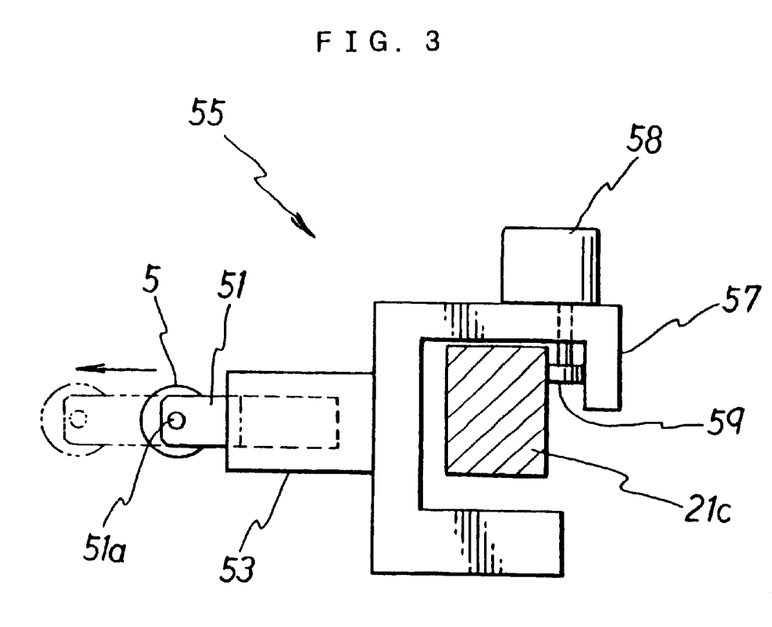
FIG. 3 shows a schematic arrangement of a pressing section for pressing the back of the human body, of the pressing medical treatment apparatus according to an embodiment of the present invention.

As shown in FIG. 3, the pressing section 55 includes a roller 5 for pressing the back of the human body, a piston 51, a pneumatic or hydraulic cylinder 53, and a pressing section-engaging section 57 for supporting the cylinder 53. The piston 51 includes, at its tip, a bearing 51a for rotatably supporting the roller 5. As shown by phantom lines in the drawing, the piston 51 is expandable from the cylinder 53, for example, in accordance with the hydraulic or pneumatic control. When the piston 51 protrudes from the cylinder 53, the pressing roller 5, which is attached to the tip of the piston 51, urges the back of the human body. The affected part can be pressed by moving the pressing section 55 in a desired direction in this state. For example, the roller 5 may be a columnar roller made of plastic or wood approximately having a diameter of 8 cm and a length of 12 cm. FIG. 11 shows a front view and a side view of a preferred columnar roller 5. The columnar roller 5 is made of urethane rubber with a recess 111 which is provided in the circumferential direction on its side wall 110. The pressing treatment is performed so that the ridge portion corresponding to the spinous process coincides with the recess 111. The pressing section-engaging section 57 is slidably engaged with a guide 21c as described later on. The pressing section 55 further comprises a friction roller 59 which makes rotation while urging the side surface of the guide 21c. The friction roller 59 is rotated by a motor 58 which is secured to the upper surface of the pressing section-engaging section 57. The pressing section 55 is movable on the guide 21c in accordance with the rotation of the friction roller 59.

Figure 4:
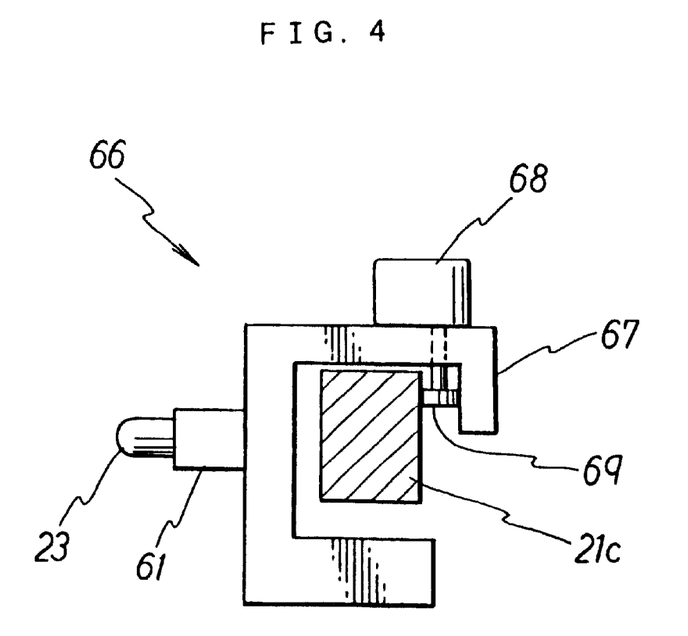
FIG. 4 shows a schematic arrangement of a detecting section for detecting the position of the specified region to be pressed, of the pressing medical treatment apparatus according to the embodiment of the present invention.

Next, the detecting section 66 will be explained with reference to FIG. 4. As shown in FIG. 4, the detecting section 66 comprises a pressure sensitive sensor 23 for detecting the spinous process, a sensor-connecting section 61, and a detecting section-engaging section 67. The pressure sensitive sensor 23 is composed of a piezoelectric element. The shape of the pressure sensitive sensor 23 is a rectangular parallelepiped with a front surface section 103 which is a curved surface as shown in FIG. 10. The front surface section is a surface to make contact with the back surface of the human body. The dimension of the pressure sensitive sensor 23 is D=1.3 cm×H=1.3 cm×L=3 cm. The pressure sensitive sensor 23 is capable of detecting the ridge corresponding to the spinous process of the thoracic vertebra protruding on the back surface of the human body by being moved while urging the back surface of the human body. The sensor-connecting section 61 may be composed of a piston and a cylinder as in the pressing section 55 shown in FIG. 3. Accordingly, the sensor-connecting section 61 may be constructed so that the pressure sensitive sensor 23 is movable frontwardly or rearwardly with respect to the detecting section-engaging section 67. The frontwardly movable distance or the rearwardly movable distance of the pressure sensitive sensor 23 is adjusted with respect to the detecting section-engaging section 67 so that the pressure sensitive sensor 23 also contacts with the inclined surface of the neck of the patient when the patient deeply bends the neck frontwardly when the spinous process of the seventh cervical vertebra is detected. The detecting section-engaging section 67 is slidably engaged with the guide 21c as described later on. The detecting section 66 further comprises a friction roller 69 which makes rotation while urging the side surface of the guide 21c. A motor 68 for rotating the friction roller is provided on the upper surface of the detecting section-engaging section 67. The detecting section 66 is movable on the guide 21c in accordance with the rotation of the friction roller 69.

With reference to FIG. 2 again, the guide section 21 includes a pair of guides 21a, 21b which extend in the direction of the body height of the patient (Z direction in the drawing), and a movable guide 21c which is movable along the guides 21a, 21b and which extends in the horizontal direction (X direction in the drawing). The movable guide 21c includes sliders 21d, 21e which are disposed at both ends thereof. The sliders 21d, 21e are engaged with the guides 21a, 21b respectively, and they are slidable thereon. Each of the sliders 21d, 21e includes a friction roller and a motor (not shown) as those shown in FIG. 3. The sliders 21d, 21e are slidable on the guides 21a, 21b. Owing to the arrangement as described above, the movable guide 21c is freely movable in the Z axis direction in FIG. 2. The pressing section 55 and the detecting section 66 are movable in the X axis direction in the drawing on the movable guide 21c by the aid of the friction rollers 59, 69 and the motors 58, 68 corresponding thereto. Accordingly, in combination with the movement in the Z direction of the movable guide 21c itself, the pressing section 55 and the detecting section 66 are freely movable in the X axis direction and the Z axis direction. That is, the pressing roller 5 and the pressure sensitive sensor 23, which are provided on the pressing section 55 and the detecting section 66 respectively, are freely displaceable on the back of the patient. The displacement amount and the position can be specified by managing the rotation or the stepping amount of the motor 58 of the pressing section 55, the motor 68 of the detecting section 66, and the motors of the sliders 21d, 21e. Alternatively, an optical encoder may be provided on the guides 21a, 21b, 21c to detect the positions of the pressing section 55 and the detecting section 66.

With reference to FIG. 1 again, a backrest surface 11 for making contact with the back of the patient is provided on one surface of the frame 12 of the main body 1. The backrest surface 11 is formed of a cover sheet having flexibility or elasticity. That is, the back of the patient can be pressed via the cover sheet by means of the roller 5 of the pressing section 55, and it can be detected by the aid of the pressure sensitive sensor 23 of the detecting section 66.

The control unit 9 is electrically connected with the cylinder 53 and the motor 58 of the pressing section 55, the sensor 23 and the motor 68 of the detecting section 66, and the motors (not shown) of the sliders 21e, 21d. The control unit can be used to move the pressing section 55 and the detecting section 66 so that the pressing roller 5 and the pressure sensitive sensor 23 installed thereto may be moved to desired positions.

The pressing medical treatment apparatus of the present invention further comprises a calculating circuit 25 which is included in the main body. The calculating circuit 25 receives a detection signal generated by the pressure sensitive sensor 23 when the spinous process of the thoracic vertebra is detected, making it possible to estimate and determine the position of the undetected spinous process of the thoracic vertebra. The calculating circuit 25 may be incorporated into the control unit 9.

Explanation will be made below for a method for performing the pressing medical treatment by using the pressing medical treatment apparatus 10 constructed as described above. At first, the patient is seated on the chair 3. The both shoulders of the patient are fixed by the shoulder holders 2. Subsequently, the neck of the patient is deeply bent frontwardly as shown in FIG. 8. The detecting section 66 is moved in the widthwise direction (X direction) on the back surface of the human body in a state in which the pressure sensitive sensor 23 is urged against the back of the human body via the cover sheet of the backrest surface 11. The movement may be performed such that the detecting section is moved reciprocatively in the X direction while changing the position in the Z direction little by little. Accordingly, at least one of the spinous processes of the first to twelfth thoracic vertebras is detected. The position of the sensor in the X direction, at which the detection signal is obtained, is read by the control unit, and the position is stored in the memory in the control unit. The position is the position of the vertebral column in the X direction of the back of the human body. Subsequently, the detecting section is moved onto the inclined surface of the cervical part, while the position in the X direction of the detecting section is fixed at the foregoing position. Alternatively, the pressure sensitive sensor 23 may be directly moved to the center of the cervical part in the X direction, because the position of the vertebral column (position in the X direction) can be estimated relatively easily from the cervical part. The detecting section is moved in the −Z direction, i.e., downwardly along the vertebral column to detect the seventh spinous process of the cervical vertebra. As shown in FIG. 8, the seventh spinous process of the cervical vertebra conspicuously protrudes on the inclined surface of the cervical part. Therefore, the seventh spinous process of the cervical vertebra can be detected and distinguished from other regions relatively easily. The spinous process of the first thoracic vertebra exists just under the spinous process of the seventh cervical vertebra. Accordingly, the detecting section is further moved downwardly to detect the spinous process of the first thoracic vertebra, the spinous process of the second thoracic vertebra, the spinous process of the third thoracic vertebra and so forth. The positions (X, Z), at which the detection signals are obtained, are successively stored with the control unit 9 respectively. Accordingly, the positions of the spinous processes of the first to twelfth thoracic vertebras are specified. As described above, the position of the spinous process corresponds to the position of the thoracic vertebra disposed just under the thoracic vertebra to which the concerning spinous process belongs. Therefore, the position information on the respective spinous processes of the thoracic vertebras is stored again as position information on the thoracic vertebra disposed just under the thoracic vertebra to which each of the spinous processes belongs.

Next, explanation will be made for the operation for pressing the specified thoracic vertebra or the zygapophyseal joint of the thoracic vertebra as the affected part on the basis of the position of the thoracic vertebra stored as described above. When it is considered that the disease of the patient is caused by the damage of the joint between the third and fourth vertebras or the damage of the joint between the fourth and fifth vertebras of the thoracic vertebra, the roller 5 of the pressing section 55 is moved to the stored position of the third and fourth thoracic vertebras. Subsequently, the piston 51 of the pressing section 55 is allowed to protrude so that the roller 5 is urged toward the back of the human body. While the roller 5 is urged against the back of the human body at a constant pressure, the movable guide 21c is slidably moved in the −Z direction, i.e., downwardly to rotate and move the roller 5 from the position of the third thoracic vertebra to the position of the fourth thoracic vertebra or from the position of the fourth thoracic vertebra to the position of the fifth thoracic vertebra. When the roller 5 is moved to the position of the fourth thoracic vertebra or the fifth thoracic vertebra, the piston 51 is retracted into the cylinder 53 so that the urging operation against the back of the human body is stopped. The roller 5 is moved again toward the position of the third thoracic vertebra or the fourth thoracic vertebra, i.e., upwardly. The pressing medical treatment can be performed for the region between the third thoracic vertebra and the fourth thoracic vertebra or between the fourth thoracic vertebra and the fifth thoracic vertebra by repeating the operation as described above. Accordingly, the torsion of the joint between the third thoracic vertebra and the fourth thoracic vertebra or the joint between the fourth thoracic vertebra and the fifth thoracic vertebra is redressed. When it is considered that the disease of the patient is caused by the damage of the joint between the tenth thoracic vertebra and the eleventh thoracic vertebra or the damage of the joint between the eleventh thoracic vertebra and the twelfth thoracic vertebra, the movable guide 21c may be slidably moved in the −z direction to move the roller 5 to the position of the tenth thoracic vertebra or the eleventh thoracic vertebra so that the pressing medical treatment is performed in the same manner as described above.

Second Embodiment

The inferior angle of scapular is detected by using the same pressing medical treatment apparatus as the pressing medical treatment apparatus described in the first embodiment to specify the position of the spinous process of each of the thoracic vertebras on the basis of the detected position of the inferior angle of scapular. In this embodiment, explanation will be made for only a method for detecting the inferior angle of scapular and a method for specifying the position of the spinous process of each of the thoracic vertebras on the basis of the detected inferior angle of scapular. The other procedures are the same as those described in the first embodiment.

As shown in FIG. 1, at first, the patient is seated on the chair 3, and the both shoulders of the patient are fixed with the shoulder holders 2, in the same manner as in the first embodiment. Subsequently, the detecting section 66 is moved in the body height direction (Z direction) on the back surface of the human body in a state in which the pressure sensitive sensor 23 is urged against the back of the human body via the cover sheet of the backrest surface 11. The movement may be performed such that the detecting section is moved reciprocatively in the Z direction while changing the X coordinate position little by little. Alternatively, the following procedure is also available. That is, the reference data XD, which indicates the presence of the inferior angle of scapular disposed at the position depending on the degree of separation in the X direction from the X coordinate position of the vertebral column on the basis of the body type of the patient, is previously stored in the memory of the control unit. The reference data XD corresponding to the body type of the patient is selected from the memory to use it so that the detecting section is moved by XD in the X direction from the position of the vertebral column. The detection of the position of the inferior angle of scapular in the Z direction is started therefrom. In this case, the reference data may function as an electronic case record, and it may be stored as data for each patient.

Thus, the inferior angle of scapular is detected in accordance with the movement of the pressure sensitive sensor 23. The inferior angle of scapular protrudes at the right and the left of the back surface of the patient. Therefore, it is relatively easy to detect and distinguish the inferior angle of scapular from other regions. The control unit 9 reads the position of the sensor 23, for example, the position (Xk, Zk) (position of the inferior angle of scapular) at which the detection signal is obtained. The position is stored in the memory. Subsequently, the spinous process of the thoracic vertebra is detected by moving the detecting section 55 in the X direction (widthwise direction of the human body) while maintaining the detected position Zk in the Z direction of the inferior angle of scapular. The spinous process is also detected with ease, because it is located approximately at the center in the X direction of the back of the patient. As shown in FIG. 9, it is already known that the position in the Z direction of the inferior angle of scapular corresponds to the lower end of the spinous process of the seventh thoracic vertebra. Therefore, the spinous process detected in this procedure can be identified to be the spinous process of the seventh thoracic vertebra.

Subsequently, the spinous processes of the thoracic vertebra are detected while moving the pressure sensitive sensor 23 upwardly along the vertebral column from the position of the spinous process of the seventh thoracic vertebra. The control unit 9 stores the positions (X, Z) at which the detection signal is obtained respectively. That is, in this case, it is possible to obtain the detection signals in an order of the spinous process of the sixth thoracic vertebra, the spinous process of the fifth thoracic vertebra, the spinous process of the fourth thoracic vertebra and so forth. Accordingly, the positions of the spinous processes of the first to seventh thoracic vertebras are specified.

Subsequently, the spinous processes are detected again while moving the pressure sensitive sensor 23 downwardly along the vertebral column from the position of the spinous process of the sixth thoracic vertebra. The positions (X, Z), at which the detection signal is obtained, are stored respectively. The detected spinous processes can be successively identified to be the spinous processes of the eighth to twelfth thoracic vertebras. Therefore, the positions of the spinous processes of the eighth to twelfth thoracic vertebras are also specified. Thus, the positions of the first to twelfth thoracic vertebras and their spinous processes are specified. The position of the spinous process corresponds to the position of the thoracic vertebra disposed just under the thoracic vertebra to which the concerning spinous process belongs. Therefore, the stored position information on the respective spinous processes of the thoracic vertebras is stored again as position information on the thoracic vertebra disposed just under the thoracic vertebra to which each of the spinous processes belongs. The specified thoracic vertebra or the thoracic zygapophyseal joint, which is the affected part, is pressed to perform the medical treatment in the same manner as in the first embodiment on the basis of the respective positions of the thoracic vertebras.

Third Embodiment

The iliac crest peak is detected by using the same medical treatment apparatus as the pressing medical treatment apparatus described in the first embodiment to specify the position of the spinous process of each of the thoracic vertebras on the basis of the detected position of the iliac crest peak. In this embodiment, explanation will be made for only a method for detecting the iliac crest peak and a method for specifying the position of the spinous process of each of the thoracic vertebras on the basis of the detected iliac crest peak. The other procedures are the same as those described in the first embodiment.

At first, as shown in FIG. 1, the patient is seated on the chair 3, and the both shoulders of the patient are fixed with the shoulder holders 2, in the same manner as in the first embodiment. Subsequently, the detecting section 66 is moved in the body height direction (Z direction) on the back surface of the human body, while changing the X coordinate position little by little in a state in which the pressure sensitive sensor 23 is urged against the back of the human body via the cover sheet of the backrest surface 11 to detect the iliac crest. The iliac crest protrudes at the right and the left of the lumbar of the back surface of the patient. Therefore, it is relatively easy to detect and distinguish the iliac crest from other regions. The control unit 9 reads the position of the sensor 23, for example, the position (Xn, Zn) (position of the iliac crest) at which the detection signal is obtained. The position (Zn, Zmax) (position of the iliac crest peak), at which the value in the Z direction is maximum, is stored in the memory. Subsequently, the spinous process of the lumbar vertebra is detected by moving the detecting section 55 in the X direction (widthwise direction of the human body) while maintaining the detected position Zmax in the Z direction of the iliac crest peak. The spinous process is also detected with ease, because it is located approximately at the center in the X direction of the back of the patient. As shown in FIG. 9, it is already known that the position in the Z direction of the iliac crest peak approximately corresponds to the center of the spinous process of the fourth lumbar vertebra. Therefore, the spinous process detected in this procedure can be identified to be the spinous process of the fourth lumbar vertebra.

Subsequently, the spinous processes of the lumbar vertebra are detected while moving the pressure sensitive sensor 23 upwardly along the vertebral column from the position of the spinous process of the fourth lumbar vertebra. The control unit 9 stores the positions (X, Z) at which the detection signal is obtained respectively. That is, in this case, it is possible to obtain the detection signals in an order of the spinous process of the third lumbar vertebra, the spinous process of the second lumbar vertebra, the spinous process of the first lumbar vertebra and so forth. The bone, which is disposed just over the first lumbar vertebra, is the twelfth thoracic vertebra. Therefore, the detection signal is successively obtained for the spinous process of the twelfth thoracic vertebra, the spinous process of the eleventh thoracic vertebra and so forth, as well as the spinous process of the second thoracic vertebra and the spinous process of the first thoracic vertebra, while further moving the pressure sensitive sensor 23 upwardly. Thus, the positions of the first to twelfth thoracic vertebras and their spinous processes are specified. The position of the spinous process corresponds to the position of the thoracic vertebra disposed just under the thoracic vertebra to which the concerning spinous process belongs. Therefore, the stored position information on the respective spinous processes of the thoracic vertebras is stored again as position information on the thoracic vertebra disposed just under the thoracic vertebra to which each of the spinous processes belongs. The specified thoracic vertebra or the thoracic zygapophyseal joint, which is the affected part, is pressed to perform the medical treatment in the same manner as in the first embodiment on the basis of the respective positions of the thoracic vertebras.

Fourth Embodiment

The pressing medical treatment is performed by using the same pressing medical treatment apparatus as the pressing medical treatment apparatus described in the first embodiment except that an infrared ray sensor is used in place of the pressure sensitive sensor. The infrared ray sensor is provided in the detecting section 66 in place of the pressure sensitive sensor 23 shown in FIG. 2. The infrared ray sensor is movable over the back of the human body, and it is capable of detecting the heat from respective regions.

At first, before the pressing medical treatment is performed by using the pressing medical treatment apparatus, the region to be pressed on the back of the human body is specified by means of examination by touch by a therapist. A heat-insulating seal is stuck to the concerning region. Subsequently, while maintaining the state in which the heat-insulating seal is stuck to the back of the human body, the patient is seated on the chair 3, and the both shoulders of the patient are fixed by the shoulder holders 2, in the same manner as in the first embodiment. In a state in which the infrared ray sensor is urged against the back of the human body via the cover sheet of the backrest surface 11, the detecting section 66 is reciprocatively moved in the body height direction (Z direction) on the back surface of the human body while changing the X coordinate position little by little to detect the portion of the back surface of the human body at which the temperature is low. The heat-insulating seal is composed of a heat-insulating material. Therefore, the portion, on which the seal is stuck, is blocked from radiation of heat from the human body, and it has a temperature lower than those of other regions. Accordingly, the concerning portion can be detected relatively easily. The control unit 9 reads the position of the infrared ray sensor, for example, the position (Xm, Zm) (position of the seal) at which the detection signal is obtained. The position is stored in the memory. The pressing member is moved to the stored position (Xm, Zm) of the seal, i.e., the region specified by the therapist to perform the pressing treatment. Thus, the pressing medical treatment can be performed instead of the therapist.

The embodiments of the present invention have been explained above with reference to the drawings. However, the present invention is not limited thereto. For example, in the second embodiment described above, the inferior angle of scapular and the spinous process of the thoracic vertebra are detected with the same pressure sensitive sensor. However, the inferior angle of scapular may be detected with a sensor having a shape suitable to detect the inferior angle of scapular. In the third embodiment described above, the iliac crest and the spinous processes of the lumbar vertebra and the thoracic vertebra are detected with the same pressure sensitive sensor. However, the iliac crest may be detected with a sensor having a shape suitable to detect the iliac crest. In the fourth embodiment described above, the mark having the heat-insulating property is detected with the infrared ray sensor. However, a mark having a light-reflecting property may be detected with an optical detector, or a mark composed of a magnetic material may be detected with a magnetic sensor.

The number of the pressing section for pressing the back of the human body is not limited to one. Two pressing sections, for example, a pressing section for pressing the upper thoracic vertebras (third, fourth, and fifth thoracic vertebras) and a pressing section for pressing the lower thoracic vertebras (tenth, eleventh, and twelfth thoracic vertebras) may be provided in the main body. In this case, the back of the human body may be simultaneously pressed with both of the rollers, or it may be pressed in a separate manner.

The apparatus may further comprise an image display unit which is capable of displaying the thoracic vertebra position with an image on the basis of the position information on the thoracic vertebra obtained by the measuring unit for measuring the position of the thoracic vertebra, a control circuit which makes it possible to externally input the region intended to be pressed so that the pressing medical treatment is performed, and a timer circuit which makes it possible to set the time for the pressing medical treatment.

The embodiments described above are based on the use of the roller as the pressing member. However, there is no limitation thereto. It is possible to use pressing members having a variety of shapes. In the embodiments described above, the pressing roller is moved on the back of the patient by using the guide and the like. However, it is also preferable to use a plurality of fixed type pressing members. For example, a plurality of pressing members, which are capable of making protrusion toward the back of the patient, are arranged in a grid-shaped configuration over the back surface so that the pressing member corresponding to the specified region is allowed to make protrusion. Alternatively, the spinous process detection sensor, the inferior angle of scapular detection sensor, the iliac crest detection sensor, and/or the infrared ray sensor may be incorporated into the pressing member itself.

INDUSTRIAL APPLICABILITY

The pressing medical treatment apparatus of the present invention is provided with the measuring unit which makes it possible to measure the position of the thoracic vertebra by detecting at least one of the spinous process of the cervical vertebra, the spinous process of the thoracic vertebra, and the spinous process of the lumbar vertebra. Therefore, the specified region of the thoracic vertebra can be automatically detected without relying on the examination by touch by the therapist. The control unit controls the operation of the pressing member so that the pressing member is moved to the specified region of the thoracic vertebra to press the concerning region on the basis of the position information on the thoracic vertebra measured by the measuring unit. Therefore, it is possible to treat a variety of symptoms based on the damage of the zygapophyseal joint of the thoracic vertebra by using the medical treatment apparatus of the present invention in place of the therapist.

What is claimed is:

1. A pressing medical treatment apparatus having a pressing member for pressing a specified region of a human body, the apparatus comprising:

a measuring unit adapted to measure at least one position of first to twelfth thoracic vertebras;

a pressing member-driving unit adapted to drive the pressing member to press a back of the human body; and a control unit which controls the pressing member-driving unit to press the measured thoracic vertebra or vicinity thereof on the basis of position information on at least one of the thoracic vertebras measured by the measuring unit.

2. The pressing medical treatment apparatus according to claim 1, wherein the measuring unit includes a spinous process detection sensor adapted to detect at least one spinous process selected from spinous process of cervical vertebra, spinous process of thoracic vertebra, and spinous process of lumbar vertebra, while urging a cervical part or a back surface of the human body.

3. The pressing medical treatment apparatus according to claim 2, further comprising a calculating unit adapted to calculate and determine a position of other spinous process or thoracic vertebra on the basis of a position of the detected spinous process.

4. The pressing medical treatment apparatus according to claim 2, wherein the spinous process detection sensor is adapted to measure a position of at least one of first to twelfth thoracic vertebras by detecting spinous process of seventh thoracic vertebra.

5. The pressing medical treatment apparatus according to claim 2, wherein the measuring unit adapted to determine a position of thoracic vertebra further comprises an inferior angle of scapular detection sensor adapted to detect inferior angle of scapular.

6. The pressing medical treatment apparatus according to claim 5, wherein a position of spinous process of seventh thoracic vertebra is determined from signals indicating respective inferior angle of scapular positions detected by the inferior angle of scapular detection sensor, and positions of the respective thoracic vertebras are determined on the basis of the position of the spinous process of the seventh thoracic vertebra.

7. The pressing medical treatment apparatus according to claim 2, wherein the measuring unit adapted to determine a position of thoracic vertebra further comprises an iliac crest sensor adapted to detect iliac crest.

8. The pressing medical treatment apparatus according to claim 7, wherein a position of spinous process of fourth lumbar vertebra is determined from signals indicating respective iliac crest positions detected by the iliac crest detection sensor, and positions of the respective thoracic vertebras are determined on the basis of the position of the spinous process of the fourth lumbar vertebra.

9. The pressing medical treatment apparatus according to claim 2, further comprising a storage unit adapted to store thoracic vertebra position information for each patient therein.

10. The pressing medical treatment apparatus according to claim 1, wherein the at least one of the thoracic vertebras is third, fourth, or fifth thoracic vertebra or tenth, eleventh, or twelfth thoracic vertebra.

11. The pressing medical treatment apparatus according to claim 1, wherein the pressing is performed in a direction from an upper half of the body to a lower half of the body along vertebral column.

12. The pressing medical treatment apparatus according to claim 1, further comprising a support member adapted to support the human body against the pressing effected by the pressing member.

13. The pressing medical treatment apparatus according to claim 1, further comprising a seat section having an adjustable height, wherein a pressing medical treatment is performed in a state in which the human body is seated thereon.

14. A pressing medical treatment apparatus having a pressing member adapted to press a specified region of a human body, the apparatus comprising:

a storage unit adapted to store thoracic vertebra position information for each patient therein;

a pressing member-driving unit which drives the pressing member to press a back of a human body; and a control unit which controls the pressing member-driving unit so that spinous process of the thoracic vertebra is pressed on the basis of the thoracic vertebra position information stored in the storage unit.

15. A pressing medical treatment apparatus having a pressing member adapted to press a specified region of a human body, the apparatus comprising:

a mark attachable to the specified region of the human body;

a detecting unit which detects the mark;

a pressing member-driving unit which drives the pressing member; and a control unit which controls the pressing member-driving unit on the basis of position information on the mark detected by the detecting unit.

* * * * *